United States Patent
Van Den Tillaart et al.

(10) Patent No.: US 12,151,987 B2
(45) Date of Patent: Nov. 26, 2024

(54) STRIPPING-TYPE UREA PLANT FOR DEF PRODUCTION

(71) Applicant: STAMICARBON B.V., Sittard (NL)

(72) Inventors: Johan Albert Arno Van Den Tillaart, Melick (NL); Eelco Mostert, Heerlen (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 18/256,554

(22) PCT Filed: Feb. 14, 2023

(86) PCT No.: PCT/NL2023/050067
§ 371 (c)(1),
(2) Date: Jun. 8, 2023

(87) PCT Pub. No.: WO2023/158303
PCT Pub. Date: Aug. 24, 2023

(65) Prior Publication Data
US 2024/0059623 A1 Feb. 22, 2024

(30) Foreign Application Priority Data
Feb. 15, 2022 (EP) ..................... 22156838

(51) Int. Cl.
*C05C 9/00* (2006.01)
*C05G 5/23* (2020.01)
*C07C 273/04* (2006.01)
*C07C 273/16* (2006.01)

(52) U.S. Cl.
CPC ............... *C05C 9/00* (2013.01); *C05G 5/23* (2020.02); *C07C 273/04* (2013.01); *C07C 273/16* (2013.01)

(58) Field of Classification Search
None
See application file for complete search history.

(56) References Cited

U.S. PATENT DOCUMENTS

| | | | |
|---|---|---|---|
| 2004/0116743 A1 | 6/2004 | Mennen | |
| 2010/0063321 A1 | 3/2010 | Zardi et al. | |
| 2013/0207035 A1 | 8/2013 | Meessen | |
| 2017/0204054 A1* | 7/2017 | Mennen | C07C 273/16 |
| 2018/0071653 A1 | 3/2018 | Dobree et al. | |
| 2018/0195158 A1 | 7/2018 | Gullberg et al. | |
| 2019/0185422 A1 | 6/2019 | Pustjens et al. | |

FOREIGN PATENT DOCUMENTS

| | | | | |
|---|---|---|---|---|
| CA | 2627827 | * | 9/2008 | ......... C05C 9/00 |
| EP | 3398935 A1 | * | 11/2018 | ......... C07C 273/14 |
| EP | 3782979 A1 | * | 2/2021 | ......... C07C 273/04 |
| EP | 3862345 A1 | | 8/2021 | |
| WO | 2017192031 A1 | | 11/2017 | |
| WO | WO 2019/093891 A1 | * | 5/2019 | ......... C07C 273/04 |
| WO | WO 2020/130817 A1 | * | 6/2020 | ......... C07C 273/04 |

OTHER PUBLICATIONS

Ullmann's Encyclopedia of Industrial Chemistry, chapter Urea, 2010.

* cited by examiner

*Primary Examiner* — Wayne A Langel
(74) *Attorney, Agent, or Firm* — Leason Ellis LLP (57) ABSTRACT

A urea plant and urea production process of the stripping type are provided that are adapted for making Diesel Exhaust Fluid (DEF) or precursor thereof in a DEF production unit downstream of a treatment section. The treatment section receives a part of the urea synthesis stream from a reaction zone, in particular bypassing the HP stripper.

19 Claims, 2 Drawing Sheets

STRIPPING-TYPE UREA PLANT FOR DEF PRODUCTION

CROSS-REFERENCE TO RELATED PATENT APPLICATIONS

This application is a U.S. National Stage Application under 35 U.S.C. § 371 of International Patent Application No. PCT/NL2023/050067 filed Feb. 14, 2023, which claims the benefit of priority of European Patent Application No. 22156838.9 filed Feb. 15, 2022, both of which are incorporated by reference in their entireties.

FIELD

The invention pertains to the production of urea, in particular to the production of highly pure urea solution suitable for instance for use as Diesel Exhaust Fluid (DEF), in a urea plant of the stripping type.

INTRODUCTION

Urea is often produced in fertilizer-grade quality. Higher purity urea products are necessary e.g. for use for $NO_x$ abatement from combustion exhaust gases, such as for the production of Diesel Exhaust Fluid (DEF). A standard for DEF is ISO 22241-1:2006 (version of 15 Oct. 2006). DEF should have low biuret content. DEF refers to an aqueous solution of urea for use in the selective catalytic reduction of $NO_x$ from exhaust gas (SCR solution).

Urea products with low biuret content can be prepared e.g. by crystallization from a mother liquor. The urea crystals can be dissolved to produce DEF.

Ullmann's Encyclopedia of Industrial Chemistry, chapter Urea, 2010, describes various urea production processes including preparation of urea with low biuret content using crystallization, and stripping processes such as the Stamicarbon $CO_2$ stripping process.

Many existing urea plants are of the stripping type with a high pressure stripper in the synthesis section, e.g. a $CO_2$ stripper or a thermal stripper.

US 2013/207035 A1 describes a process wherein a first urea-comprising aqueous stream is taken directly from or after a recovery section in a urea production process and diluted. The recovery section is arranged downstream of the synthesis section.

US 2017/204054 A1 describes a process for making DEF using flash crystallization.

US 2018/0071653 A1 describes a method comprising stripping urea reaction solution and diluting a part of an aqueous urea stream with water to obtain a solution suitable for use in a unit for the reduction of $NO_x$.

EP 3862345 A1 of Casale describes a process for purifying a urea-containing aqueous stream comprising a step of removing biuret from the urea-containing stream by reverse osmosis, for making SCR solution.

The present invention is directed to the production in a urea plant of the stripping type of a urea product suitable for use as DEF, or suitable as DEF precursor, in particular to the production of a urea product that is suitable to be diluted by adding water to form DEF. DEF precursor is typically converted into DEF outside the urea plant by adding sufficiently pure water. It remains challenging to produce DEF or DEF precursor urea product with sufficiently high purity in urea plants of the stripping type.

DEF is used in vehicles with diesel engines for $NO_x$ emissions abatement. The composition of DEF for vehicles is standardized in ISO 22241-1:2006. DEF for vehicles has about 32.5 wt. % urea (i.e. essentially the eutectic composition) and also has very low concentration of impurities. The product urea solution can also be used e.g. for $NO_x$ abatement in industrial plants and in ships and trains. For $NO_x$ abatement used in rail and marine applications, about 40 wt. % urea solution is used according to ISO 186111-1: 2014. For $NO_x$ abatement for (fossil fuel) power plants, typically 50 wt. % urea solution is used. The term "DEF" is used in the present disclosure, also for the invention, to refer in particular to a urea solution suitable, adapted and/or identified for use in $NO_x$ abatement, e.g. urea solution according to any of said specifications, more in particular to urea solution according to ISO 22241-1:2006.

When making DEF, the concentration of urea is important in order to allow accurate dosing of the liquid to the SCR catalyst. The low concentration of organic impurities in DEF is important to avoid clogging and coke formation on the catalyst surface. The very low concentration of inorganic impurities in DEF, in particular of heavy metals, is important because these impurities contribute to poisoning of the SCR catalyst. The metals will accumulate on the catalyst and thereby reduce the lifetime of the catalyst.

In the referenced specifications for DEF, the maximum limits for metal impurities are close to the typical achievable concentrations in urea streams obtained from a typical urea stripping plant. In particular, during upset conditions or start-up conditions the amounts of metal in the urea solution from urea stripping plants frequently may exceed DEF specifications. In the case of a urea plant which is designed specifically for only DEF production and no solid urea production (e.g. a plant without urea solidification section) this may lead to significant amounts of urea material that is outside the product specifications and which cannot be handled in the plant (e.g. inside battery limits).

US 20040116743 A1 describes a urea plant with a high pressure (HP) stripper receiving a first part of the urea synthesis solution; a second part is supplied to a medium pressure (MP) dissociator and a medium pressure (MP) stripper and subsequently to a low pressure (LP) recovery section which also receives stripped urea solution from the HP stripper.

Jan Mennen, Nitrogen 2005, "The MEGA urea plant concept is now reality at SKW Piesteritz, Germany" illustrates a urea production process wherein a first part of the urea solution from the urea reactor is supplied to a HP stripper using $CO_2$ strip gas, and a second part is supplied to an MP dissociator, urea solution from the HP stripper and the MP dissociator are combined and supplied to a low pressure (LP) rectifier.

EP 2086928 B1 describes a process wherein a first part of the urea solution from the urea reactor is supplied to a HP stripper and a second part is supplied to an MP dissociator, wherein urea solution from the HP stripper and from the MP dissociator are combined and sent to an LP recovery section.

SUMMARY

The invention pertains in a first aspect to a urea production plant for producing a first urea-containing product and a second urea-containing product, wherein the second urea-containing product is Diesel Exhaust Fluid (DEF) or DEF precursor, the plant comprising a high pressure (HP) synthesis section comprising a reaction zone, a high pressure (HP) stripper, a condensation zone, and a flow splitter adapted for dividing a urea synthesis stream from said reaction zone into a first stream and a second stream, and a flow line for said first stream to said HP stripper, the plant further comprising: a urea processing section for processing a stripped urea solution from said HP stripper into said first urea-containing product, the urea processing section comprising a recovery section comprising one or more recovery section decomposers for processing said stripped urea solution; an expansion device for expanding said second stream to give an expanded second stream; a treatment section comprising one or more treatment section decomposers for purifying said expanded second stream into a purified urea solution, wherein the one or more treatment section decomposers are arranged in parallel to the one or more recovery section decomposers; and preferably a DEF production unit for producing DEF and/or DEF precursor from said purified urea solution.

The invention in an aspect also provides a urea production process wherein a urea synthesis stream is split into a first part and a second part, wherein the first part is stripped in a high pressure (HP) stripper, recovered in a recovery section comprising one or more recovery section decomposers, and processed into a first urea-containing product, preferably a urea fertilizer product, and wherein the second stream is sent to a treatment section comprising one or more treatment section decomposers without passing through the HP stripper, wherein the one or more treatment section decomposers operate separately from and in parallel to the one or more recovery section decomposers and wherein the treatment section produces a urea-comprising stream which is suitable for use as Diesel Exhaust Fluid or for preparation of Diesel Exhaust Fluid by dilution with water; wherein preferably no urea solution is supplied from the HP stripper to the treatment section, and wherein preferably no urea solution is supplied from the recovery section to the treatment section.

The invention also provides, in a further aspect a method of modifying an existing urea plant of the stripping type comprising a high pressure (HP) synthesis section comprising a reaction zone, a condensation zone, and a high pressure HP stripper, and a recovery section, wherein the recovery section comprises a recovery section low pressure (LP) decomposer, the method comprising adding to the existing plant: a flow splitter for dividing a urea synthesis stream from the reaction zone into a first part and a second part, the first part being supplied to the HP stripper; a treatment section for processing said second part, wherein the treatment section comprises a treatment section LP decomposer in parallel to the recovery section LP decomposer.

Any embodiments illustrated in the figures are examples only and do not limit the invention.

DETAILED DESCRIPTION

The present invention is in an aspect broadly based on the judicious insight to produce DEF in a urea plant of the stripping type by treating a part of a urea synthesis solution in a treatment section operating at medium and/or low pressure without passing through a high pressure (HP) stripper, and to process the treated urea solution into a DEF product essentially without addition of urea from the stripped urea solution. This advantageously allows for preparing high purity urea solution in the treatment section, in particular to achieve low metal content.

The invention is, in certain aspects, directed to a urea plant and to a process carried out in such a plant. The urea plant comprises a high pressure (HP) synthesis section comprising a reaction zone, a high pressure (HP) stripper, and a condensation zone. The urea plant is for instance of the $CO_2$-stripping type or the thermal stripping type.

The HP synthesis section has an inlet for $NH_3$ feed and an inlet for $CO_2$ feed. In the process urea is formed by the reaction of $NH_3$ with $CO_2$.

The reaction zone is for example provided as a vertical urea reactor, though other configurations are also possible. The vertical urea reactor for example has one or more inlets at the bottom and one or more outlets at the top or for example one or more inlets at the bottom and an outlet provided with a downcomer. The urea reactor may comprise horizontal trays to improve fluid flow in the reactor. The reactor may have one outlet for a urea synthesis stream comprising both gas and liquid, or for instance separate outlets for gas and liquid. The reaction zone and the condensation zone are for instance combined in a single vessel or for instance in a single unit, such as a so-called pool reactor, e.g. as illustrated in Ullmann's Encyclopedia, chapter Urea, 2010, FIG. 19. A pool reactor is a horizontal vessel comprising a reaction zone and a condensation zone.

One or more reactors can be used, in series or in parallel. One or more condensers can be used, for instance in series or in parallel.

The reaction zone, the condensation zone, and the stripper are operated at a pressure in the high pressure range. The reactor, the condenser, and the stripper can be operated at substantially the same pressure or at different pressures. E.g. in a self-stripping plant the reactor is typically operated at 155-160 bar and the stripper at 145-150 bar. In a $CO_2$ stripping type plant the reaction zone, the condensation zone and the stripper are e.g. all operated at the same pressure, e.g. at 138-142 bar.

The reactor outlet temperature is e.g. above 180° C., e.g. in the range 180-190° C.

The urea solution at the reactor outlet has an N/C ratio of e.g. 3.0-3.8, e.g. 3.0-3.1, in plants with a high pressure (HP) $CO_2$ stripper and for instance an N/C ratio of e.g. 3.3-3.6 in plants with a high pressure (HP) thermal stripper.

The synthesis section may comprise further HP units, such as a high pressure (HP) scrubber, or a pre-reactor, or an ejector.

The HP stripper receives a part, but not all, of the urea solution comprised in the urea synthesis stream from the reactor. In particular, the HP stripper receives the first stream from a flow splitter. The urea solution received by the HP stripper also comprises carbamate.

The stripper uses for instance $CO_2$ as a strip gas or uses thermal stripping (self-stripping). The stripper is typically a shell-and-tube heat exchanger, with the urea solution as a falling film in the tubes and a heating fluid, typically steam, in the shell side space. The gas outlet of the stripper is connected to the condensation zone. All or a part of the gas from the stripper is supplied to the condensation zone. In some embodiments, a part of the gas from the stripper is supplied to the reactor to improve the heat balance in the reactor. The stripper has an inlet for the urea synthesis solution and an outlet for the stripped urea solution. A stripper of the $CO_2$ stripping type for instance has an inlet for the urea synthesis solution at the top, a gas outlet at the top, an inlet for $CO_2$ used as a strip gas at the bottom, and an outlet for the stripped urea solution at the bottom, all connected to the stripper tubes; as well as an inlet and outlet for a heating fluid at the shell side.

The invention is especially, but without limitation, suitable in embodiments wherein the stripping in the HP synthesis section is carried out using steam with a temperature of at least 195° C., e.g. 195-225° C., and/or for instance with saturated steam at 14-24 bar absolute.

The stripper tubes are for instance made of corrosion-resistant materials, for example stainless steel alloys, in particular ferritic-austenitic duplex stainless steel. Example duplex steel alloys are described in WO 95/00674 A1, WO 2017/013180 A1 and WO 2017/014632 A1. The parts of the reactor in contact with the reaction mixture are preferably also made of duplex stainless steel, more preferably of the duplex steel alloys as described. This contributes to low metal content of the urea synthesis solution.

In a particular embodiment, the stripper is a $CO_2$ stripper comprising stripper tubes made of duplex ferritic-austenitic stainless steel.

Suitable duplex stainless steel for the stripper tubes include for example the steel available as Safurex® steel and having composition 29Cr-6.5Ni-2Mo—N, which steel is also designated by UNS S32906, or e.g. the steel available as DP28W™ steel and having composition 27Cr-7.6Ni-1 Mo-2.3W—N, which is also designated by ASME Code 2496-1 and by UNS 532808. The duplex steel for the stripper tubes has for instance the composition (% by mass): C: max. 0.05; Si: max. 0.8; Mn: 0.3-4.0; Cr: 28-35; Ni: 3-10; Mo: 1.0-4.0; N: 0.2-0.6; Cu: max. 1.0; W: max. 2.0; S: max. 0.01; Ce: 0-0.2; balance Fe and (unavoidable) impurities. Preferably, the ferrite content is 30-70% by volume and more preferably 30-55%. More preferably, the steel contains (% by weight): C max. 0.02, Si max. 0.5, Cr 29 to 33, Mo 1.0 to 2.0, N 0.36 to 0.55, Mn 0.3 to 1.0, balance Fe and (unavoidable) impurities.

Also advantageous is the duplex stainless steel having the composition weight % (wt. %): C max. 0.030; Si max. 0.8; Mn max. 2.0; Cr 29.0 to 31.0; Ni 5.0 to 9.0; Mo less than 4.0; W less than 4.0; N 0.25-0.45; Cu max. 2.0; S max. 0.02; P max. 0.03; balance Fe and unavoidable occurring impurities; and wherein the content of Mo+W is greater than 3.0 but less than 5.0 (wt. %), preferably greater than 3.0 but less than 4.0 wt. %, furthermore preferably with a steel composition as described in WO 2017/014632 A1 which is hereby incorporated by reference.

The condensation zone, used as a high pressure (HP) carbamate condenser, is for instance provided as a vertical or horizontal HP carbamate condenser, and typically as a horizontal or vertical shell-and-tube heat exchanger for heat exchange against a cooling fluid. The gas to be condensed from the stripper is received in the tubes or in the shell-side space of the shell-and-tube heat exchanger. The condensation zone receives all or a part of the gas stream from the HP stripper, typically at least 60 vol. %, e.g. at least 90 vol. %. Optionally a part of the gas stream from the HP stripper, e.g. 5-40 vol. %, is supplied to the reaction zone.

The HP carbamate condenser has an outlet for a fluid stream comprising a liquid which comprises ammonium carbamate in the liquid. The outlet is connected, for liquid flow connection, with an inlet of the reactor. Typically carbamate recycle solution from one or more low pressure (LP) and/or medium pressure (MP) carbamate condensers included in the plant is also supplied to the part of the condenser which receives gas from the stripper. In embodiments wherein the gas is condensed in the vertical tubes of the condenser, carbamate solution is e.g. supplied to the top of the tubes (falling film) or to the bottom. In other embodiments, the gas to be condensed is supplied to the tubes of a U-shaped horizontal tube bundle (kettle type). In embodiments with the gas to be condensed in the shell side space, the condenser typically comprises a tube bundle for a cooling fluid, wherein the tube bundle is e.g. vertical or horizontal. The HP carbamate condenser for instance comprises a straight or the U-shaped tube bundle. The condenser may comprise two or more tube bundles. The cooling fluid is typically a liquid at the cooling fluid inlet of the condenser and is e.g. water used for raising steam and/or a process stream to be heated, such as urea solution also containing carbamate. Two or more cooling fluids can be used, e.g. with dedicated tube bundles. An example horizontal submerged condenser is a pool condenser is illustrated in Ullmann's Encyclopedia, 2010, chapter Urea, FIG. 18.

The liquid containing ammonium carbamate, optionally with any non-condensed gas, is supplied to the reaction zone. Optionally non-condensed gas is separated from the condensate in a gas/liquid separator and supplied to another unit e.g. to a scrubber or to an medium pressure (MP) section.

Feed $CO_2$ and feed $NH_3$ are supplied, completely or in part, directly or indirectly, to the synthesis section, e.g. in some embodiments feed $CO_2$ and $NH_3$ are both supplied to a reactor (e.g. in combination with thermal stripping). In some embodiments with HP $CO_2$ stripping, a part or all of the $CO_2$ is supplied to the stripper and a part or all of the $NH_3$ feed is supplied e.g. to the HP carbamate condenser.

The synthesis section comprises a flow splitter. The flow splitter, or divider, is adapted for dividing a urea synthesis stream from the reaction zone into a first stream, which is supplied to the HP stripper, and a second stream. Both the first stream and the second stream contain urea. In particular, the urea synthesis solution from the reaction zone is divided into the first stream and the second stream.

In some embodiments of the process, up to 50 wt. %, or e.g. up to 35 wt. %, for example 10-30 wt. %, of the urea from the reaction zone is supplied to the treatment section as the second stream. The flow splitter is for instance suitable for providing an adjustable fraction of the urea synthesis solution to the HP stripper and an adjustable fraction of the urea synthesis solution to the treatment section, e.g. a fraction ranging from no urea solution to all urea solution, to the HP stripper, or to providing simultaneously a part of the urea synthesis solution to the HP stripper and a part to the treatment section.

The first and second stream, independently, optionally are liquid streams. In some embodiments the process involves gas/liquid separation of the reaction mixture in the reaction zone upstream of the flow splitter, e.g. already in the reactor or in a gas/liquid separator between the reaction zone and the flow splitter. In such embodiments the flow splitter only receives urea synthesis solution.

The urea synthesis solution comprises urea, water, ammonium carbamate, and unconverted ammonia. The N/C ratio of the urea synthesis solution as received by the flow splitter and as received by the expansion device is preferably the same as at the outlet of the reaction zone.

Preferably, the plant comprises control means for adjusting the mass ratio of the first and the second stream. In this way, a flexible fraction of the urea synthesis solution can be supplied to the treatment section respectively to the HP stripper. For instance, when demand for fertilizer urea product is low, relatively more urea can be supplied to the treatment section for making DEF. During some periods all urea solution may be supplied to the treatment section respectively to the HP stripper.

The plant comprises a urea processing section for processing the stripped urea solution from said HP stripper into the first urea-containing product. The urea processing section comprises a recovery section and for example an evaporation section downstream of the recovery section and for example a finishing section downstream of the evaporation section.

The recovery section comprises one or more recovery section decomposers for processing the urea solution from the HP stripper, and the plant typically comprises one or more condensers connected with gas outlets of the one or more recovery section decomposers.

The term "recovery section" is used herein broadly to refer to recovery of urea from the stripped urea solution, i.e. to the processing of the stripped urea solution to remove non-urea components, such as carbamate and ammonia, at least in part. The recovery section may for instance comprise a medium pressure (MP) decomposer and a downstream low pressure (LP) decomposer in series, or for instance a LP decomposer receiving stripped urea solution directly from the HP stripper.

The decomposer is for instance a heat exchanger using a heating fluid, to decompose carbamate and remove $NH_3$ and $CO_2$. The decomposer has an outlet for gas. The decomposer is for instance a shell-and-tube heat exchanger for indirect heat exchange with the heating fluid. The heating fluid is e.g. steam or a process stream, e.g. a condensing process gas stream.

The gas stream comprising $CO_2$ and $NH_3$ from the recovery section decomposer, preferably from the MP or LP recovery section decomposer, is for example supplied to the carbamate condenser. Carbamate solution formed in the carbamate condenser is typically recycled to the reaction zone, optionally through the HP carbamate condenser. In this way, typically the recovery section is of a 'total recycle' design.

Urea solution from the decomposer may be treated further, such as with an atmospheric flash, sub-atmospheric flash, and/or in a pre-evaporator.

The recovery section for instance comprises e.g. an LP decomposer, in particular with a HP $CO_2$ stripper, with optionally in some embodiments an MP treatment unit, such as an MP adiabatic flash unit, between the outlet for stripped urea solution of the HP stripper and the inlet of the LP decomposer.

The recovery section for instance comprises a medium pressure (MP) decomposer with a downstream low pressure (LP) decomposer, for example with a HP thermal stripper.

As the term "recovery section" is used in the present disclosure, the recovery section may comprise units operating at different pressures and may e.g. comprise both an MP recovery section and an LP recovery section.

Stripped urea solution after passing through the recovery section, e.g. after passing through the LP decomposer, comprises e.g. at least 75 wt. % urea, e.g. 75 to 85 wt. % urea, and water, and biuret and metal impurities. The urea solution can be used e.g. for making urea ammonium nitrate (UAN) liquid fertilizer. In some embodiments, the plant comprises a UAN production unit downstream of the recovery section, wherein urea solution from the recovery section is mixed with ammonium nitrate (AN) solution.

The first urea-containing product of the process is e.g. the urea solution from the LP decomposer.

The urea solution is preferably converted into urea melt comprising at least 90 wt. % urea in an evaporation section for water removal. For instance at least 90 wt. %, or at least 95 wt. %, or e.g. all of the urea in the stripped urea solution is transformed into such a urea melt. The urea melt may contain e.g. at least 95 wt. % urea or at least 99 wt. % urea. The evaporation section comprises e.g. one or more vacuum evaporators.

The urea melt is e.g. subjected to urea finishing to form a solid urea product, for instance by granulation or prilling. Other uses of the urea melt are also possible, such as for melamine production. The first urea-containing product of the process is e.g. the solid urea product or the urea melt.

Water vapor removed in the evaporation section is for instance condensed and the condensate is e.g. treated in a waste water treatment (WWT) section, which comprises e.g. a hydrolyser and a desorber. Cleaned process condensate from the WWT is e.g. used for making DEF, in particular by dilution of a urea solution, and/or is for instance supplied to a low pressure (LP) carbamate condenser to avoid crystallization of carbamate.

Very elegantly, the plant optionally comprises a liquid flow connection for the urea solution from the treatment section to the evaporation section, preferably a liquid flow line for the urea solution from the treatment section to the evaporation section. For instance the plant comprises a liquid flow line from the treatment section LP decomposer to the evaporation section. Thereby an outlet of the treatment section for urea solution is connected, for liquid flow, with an inlet of the evaporation section. The treatment section is preferably also connected with an inlet of a DEF production unit by a flow line for urea solution in parallel to the flow line to the evaporation section.

The liquid flow connection can be provided for example as a flow line for urea solution from the treatment section to the recovery section, wherein the evaporation section receives urea solution from the recovery section. Preferably, the flow line is connected at the inlet of the flow line to the MP decomposer, a medium pressure (MP) contacting unit (such a medium pressure (MP) adiabatic stripper), the LP decomposer, or a residual ammonia removal unit of the treatment section. For instance, the plant comprises a flow line for urea solution from the MP decomposer or the MP contacting unit of the treatment section to an inlet of the recovery section LP decomposer. For instance the plant comprises a flow line for urea solution from the residual ammonia removal unit to an inlet of the evaporation section.

In a preferred embodiment, the plant comprises a flow line for urea solution from the treatment section to an inlet of the evaporation section. The liquid flow connection, including the preferred embodiments of the flow line, provides the advantage that in case of low demand for DEF and/or high demand for (solid) urea fertilizer, urea solution from the treatment section can be converted into urea melt. This can also be used during plant upsets wherein DEF quality may not be guaranteed but fertilizer grade urea can be securely produced. Hence, the liquid flow connection provides for improved flexibility of the plant.

Preferably, the plant comprises a liquid flow connection for urea solution from the treatment section LP decomposer to an inlet of the evaporation section and a liquid flow connection for urea solution from the treatment section LP decomposer to the preferred residual ammonia removal unit, for example with a preferred steam stripper. This provides improved flexibility, without increased load of the recovery section.

Optionally, the process involves supplying urea solution from the treatment section to the preferably used evaporation section, or for instance to the recovery section, or for instance to a UAN production section.

In yet a further embodiment, the plant comprises a flow line for urea solution from the treatment section to a UAN production unit. This similarly provides for improved flexibility.

In an embodiment, the plant is of the $CO_2$ stripping type and the HP stripper uses $CO_2$ as strip gas. Preferably, the reaction zone is operated with an N/C ratio of 3.0-3.2 (reaction zone urea solution outlet) and preferably at a pressure of 140-160 bar. Preferably, the HP reactor, HP condenser and HP stripper are operated at essentially the same pressure. Preferably, gravity flow is used for fluid transport from the condenser to the reactor and from the reactor to the stripper. Preferably, the stripper tubes are made of stainless steel, e.g. duplex austenitic-ferritic stainless steel, such as the steels discussed hereinabove.

Advantageously, since only a part of the urea formed in the reaction zone is processed in the HP stripper, a relatively larger part of the $CO_2$ feed is available for stripping, which can be used to reduce energy consumption in the HP stripper and/or to achieve high stripping efficiency. If only a part of the $CO_2$ feed is used for stripping, other parts of the $CO_2$ feed may be supplied to the reaction zone directly or be used for adjusting (decreasing) the N/C ratio in one or more carbamate condensers (N/C ratio as measured at carbamate solution outlet).

Stripped urea solution is e.g. supplied directly to the LP decomposer. The LP decomposer is operated at e.g. 2-6 bar, e.g. about 4 bar.

In some embodiments, the HP stripper is a thermal stripper and the stripper comprises stripper tubes which are e.g. bimetallic stripper tubes. Also for thermal striping, an advantage of lower metal content for the DEF production can be achieved with the process and plant of the invention. For instance, the inner tubes of bimetallic stripper tubes, made of e.g. Zr or Ti, may be liable to erosion leading to loss of metal into the stripped urea solution. Furthermore, if stainless steel stripper tubes are used, there can be loss of metal into the urea solution e.g. by passive corrosion.

In embodiments with thermal HP stripping, the recovery section typically comprises a medium pressure (MP) decomposer and a downstream low pressure (LP) decomposer. The HP synthesis section typically comprises a high pressure (HP) ejector for transporting liquid comprising carbamate from the HP condenser to a vertical urea reactor. The HP ejector typically uses feed $NH_3$ as a motive fluid. The reactor is operated e.g. with an N/C ratio of 3.2-3.6 at the reactor outlet.

The plant comprises an expansion device for expanding the second stream to give an expanded second stream, e.g. to reduce the pressure of the second stream from high pressure to medium pressure. The expansion device is e.g. an expansion valve.

The treatment section comprises one or more treatment section decomposers for purifying the expanded second stream, which comprises urea solution, into a purified urea solution. The treatment section is for processing non-stripped urea solution. The treatment section receives a part of the urea synthesis stream from the reaction zone, namely the second stream. In particular said part of the urea synthesis stream, i.e. the second stream, bypasses the HP stripper.

The treatment section for example comprises a medium pressure (MP) decomposer, a low pressure (LP) decomposer, or for example both the MP and the LP decomposer in series.

The treatment section decomposers and the recovery section decomposers are separate units. In particular, the treatment section decomposers are separate from and additional to the recovery section decomposers. The treatment section decomposers and the recovery section decomposers are arranged in parallel. Thereby mixing of urea solution from the first and the second stream can be avoided.

The one or more decomposers have an inlet for urea solution, an outlet for urea solution and an outlet for a gas stream comprising $NH_3$ and $CO_2$. In operation, at least some carbamate comprised in the urea solution is decomposed in the decomposers. The decomposers are for instance heat exchangers using a heating fluid, e.g. steam or e.g. a condensing process stream or e.g. steam condensate. The decomposers are typically shell-and-tube heat exchangers.

The gas outlet a decomposer is typically connected with the carbamate condenser. The carbamate condenser is typically a heat exchanger using a cooling fluid. The cooling fluid is e.g. water or urea solution to be heated. The carbamate condenser has an outlet for condensate and typically an outlet for non-condensed gas. Carbamate solution from the one or more carbamate condensers is recycled directly or indirectly to the reaction zone. The carbamate condensers are optionally common with the recovery section. In particular, a gas stream from a treatment section decomposer is preferably combined with a gas stream from a recovery section decomposer and the combined gas stream is subjected to condensation in a condenser; optionally one or both of these gas streams are already partly condensed before being combined.

The treatment section may comprise additional urea solution processing units operating at medium pressure and/or low pressure, such as an adiabatic flash vessel. In an exemplary embodiment, the treatment section comprises the adiabatic flash vessel and the downstream LP decomposer, optionally without the MP heat exchanger decomposer. The flash vessel has an inlet for urea solution, an outlet for urea solution, and an outlet for flash vapor. The flash vessel is arranged downstream of the expansion device such as the expansion valve or the flash vessel comprises an expansion device. The flash vessel is operated at medium pressure and used for adiabatic flashing of the urea solution from high pressure to medium pressure.

The flash vapor at medium pressure is supplied, for instance, to the MP carbamate condenser for instance also receiving fresh $CO_2$.

Preferably, no stripped urea solution (stripped in the HP stripper) is supplied to the treatment section. For example, the urea solution at the outlet of the treatment section contains less than 5 wt. % urea originating from stripped urea solution. This contributes to low metal content and low biuret content of the urea solution obtained from the treatment section.

Optionally, steam stripping, in particular with injection of steam into the urea solution, can be used to remove traces of $NH_3$ from the urea solution in the treatment section.

In embodiments wherein the treatment section comprises a treatment section LP decomposer, the treatment section LP decomposer is separate from the LP decomposer comprised in the recovery section. Hence, the treatment section LP decomposer is arranged in a parallel to the recovery section LP decomposer.

Particularly, the treatment section LP decomposer is a dedicated LP decomposer. This provides an important difference with prior art processes wherein urea solution from the HP stripper and from a medium pressure (MP) treatment section are expanded combined and the resulting combined urea solution is supplied to an LP decomposer.

In an embodiment, the treatment section comprises a medium pressure (MP) decomposer and a low pressure (LP) decomposer in series, optionally with a medium pressure (MP) contacting unit between the MP decomposer and the LP decomposer. Gas from the treatment section MP decomposer is typically condensed in a medium pressure (MP) carbamate condenser. This MP carbamate condenser may optionally also receive gas from a recovery section medium pressure (MP) decomposer.

A part of the $CO_2$ feed can be supplied to the MP carbamate condenser, to adjust the N/C ratio therein. Optionally, said part of the $CO_2$ feed is first contacted with the urea solution in the treatment section in order to adjust the N/C ratio of the urea solution, for instance in a MP contacting unit arranged in the flow line for urea solution between the MP decomposer and the LP decomposer. The MP contacting unit has an outlet for a gas stream connected to an inlet of the MP carbamate condenser. The MP contacting unit is used e.g. for MP stripping of the urea solution, more preferably for MP adiabatic stripping, and preferably is a medium pressure (MP) adiabatic stripper. The MP stripping involves counter-current flow of the gas stream in direct contact with the urea solution. The MP adiabatic stripping may contribute to sufficient condensation in a low pressure (LP) carbamate condenser connected to a low pressure (LP) decomposer receiving urea solution from the MP adiabatic stripping.

The treatment section optionally comprises, typically downstream of the LP decomposer, a residual ammonia removal unit. The residual ammonia removal unit is for example a steam stripper, or for example a stripper using an inert gas, such as $N_2$, or for example a unit operating at a lower pressure than the LP decomposer, for instance a unit operating at sub-atmospheric pressure, i.e. a pressure of less than 1.0 bar absolute. The residual ammonia removal unit is typically operated at LP (1-10 bar) or a pressure below 1.0 bar.

The residual ammonia removal unit is for example a steam stripper for processing urea solution from a treatment section decomposer, typically for processing low pressure (LP) urea solution from a low pressure (LP) treatment section decomposer. The optional steam stripper is operated e.g. at a pressure below 1.0 bar absolute. The steam stripper is for instance a vessel having an inlet for steam and configured for injecting steam into the urea solution. The steam stripper can be used to control and reduce the amount of $NH_3$ in the DEF precursor; other units and methods can also be used to control and reduce the amount of $NH_3$ in the DEF precursor. The urea solution at the liquid outlet of the steam stripper for example meets the DEF specification and for instance $NH_3$ is max. 0.2 wt. %, e.g. alkalinity as $NH_3$ is max. 0.2 wt. % in the urea solution at the liquid outlet of the steam stripper. Other purification devices may also be used and in some embodiments the urea solution obtained from a treatment section decomposer already meets the DEF specification.

The plant further comprises, downstream of the treatment section, preferably a DEF production unit. The DEF production is unit is a preferred part of the plant and is preferably also used in the urea production process.

The DEF production unit is for instance a dilution unit configured for adding water to the purified urea solution obtained from the treatment section to obtain the desired urea concentration. In particular high purity water is added, e.g. clean process condensate such as from a waste water treatment section of the urea plant. In principle, dilution water can additionally or alternatively be added upstream in the process, but this is generally less preferred in view of the purification step.

In some embodiments, the DEF production unit comprises a dry flashing unit, e.g. as described in US 2017/204054A1.

The dry flashing unit comprises a liquid distributor, in particular a spray nozzle. The dry flashing, is preferably conducted at a pressure below 15 kPa, preferably in the range 1 to 10 kPa. Preferably, the urea solution subjected to dry flashing has a urea concentration in a range of from 85 wt. % to 95 wt. %, more preferably between 87 wt. % and 92 wt. %. The DEF production unit may comprise an evaporator to increase the urea concentration of the urea solution upstream of the dry flashing unit. Typically, in embodiments wherein the DEF production unit comprises a dry flashing unit, the treatment section contains no residual ammonia removal unit, for instance no steam stripper. The dry flashing, preferably yields a free-flowing urea powder. Preferably, the DEF production unit comprises a packaging unit to pack the powder, e.g. a bagging unit. Preferably, the free-flowing urea powder is packaged with a moisture content below 0.2 wt. % and preferably in non water-permeable packaging. Preferably, the plant comprises a conveying line for conveying the powder from the dry flashing unit, to the packaging unit. The powder can be easily transported, easily packaged and subsequently easily removed from its package, and can be dissolved in order to produce DEF.

By supplying the second stream from the reaction zone to the treatment section without HP stripping, the urea solution can have a lower metal content. In particular, the processing of the second stream involves less corrosive process conditions than HP stripping. The intermediate reaction product ammonium carbamate, contained in the urea synthesis solution, is extremely corrosive especially at high temperature such as in a high pressure stripper. In particular, in a stripping plant, the reactor can operate at e.g. about 185° C. but the peak temperatures at the top of the HP stripper are e.g. at 210-220° C. Furthermore, HP strippers are typically shell-and-tube heat exchangers with urea solution in the stripper tubes and steam on the shell side, and in the HP stripper the amount of metal surface in contact with ammonium carbamate containing urea solution is high due the large number of tubes.

The lower metal content of the urea synthesis solution as source for the second-urea containing product is important for use as DEF and as reductant in $NO_x$ abatement systems, because these systems contain an (expensive) catalyst for selective catalytic reduction. Presence of metallic species in the urea solution decreases the life time of the selective catalytic reduction (SCR) catalyst because of metal accumulation. Reducing the metal content (i.e. metal concentration) will consequently lead to a longer lifetime of the SCR catalyst.

Biuret is a disadvantageous component in the urea used for selective catalytic reduction (SCR) systems since exposure of the biuret component to the catalyst causes isocyanuric acid formation that decreases the life time of the SCR catalyst. Therefore a lower biuret content in the supplied urea solid to be used for i.e. DEF solution extends the lifetime of the SCR catalyst.

DEF produced in the DEF production unit will have a significantly lower biuret and metal content compared to a process wherein the DEF production unit receives urea solution from the recovery section, because the precursor solution for production of DEF in the invention has not been exposed to the typical high temperature conditions in the HP stripper and therefore the process avoids the biuret formation and corrosion resulting from these conditions.

The first urea-containing product obtained from the urea processing section, and also with the inventive urea production process, is e.g. a final product, such as solid urea product, or e.g. an intermediate product, such as urea melt that can be used for melamine production, or urea solution that can be used for UAN production. The first urea-containing product is preferably fertilizer grade urea.

The second urea-containing product, which is typically obtained downstream of the treatment section in the DEF production unit, is preferably Diesel Exhaust Fluid (DEF) or DEF precursor. DEF precursor indicates urea product that can converted into DEF by adding (pure) water.

DEF indicates broadly a urea solution suitable for catalytic selective reduction of $NO_x$, i.e. for $NO_x$ abatement.

The high purity urea solution obtained from the treatment section is used for making DEF or DEF precursor. For instance, by diluting the urea solution with water to a desired target urea concentration, e.g. to about 32.5 wt. % urea for DEF according to ISO 22241-1:2006, to about 40 wt. % urea solution according to ISO 186111-1:2014, or e.g. to about 50 wt. % urea solution for $NO_x$ abatement in industrial plants.

The purified urea solution from the treatment section and the DEF product and/or the DEF precursor product, e.g. from the DEF production unit, has low impurities. The same applies for the urea-comprising stream suitable for use as or for preparation of DEF prepared in the inventive process. Preferably, the impurities are in agreement with envisaged use as DEF or for the dilution to DEF by adding water, particularly DEF in compliance with ISO 22241-1:2006 (i.e. with 32.5 wt. % urea) and/or ISO 186111-1:2014. Generally, biuret is max 0.3 wt. %. Generally, $NH_3$ is max. 0.2 wt. %, e.g. alkalinity as $NH_3$ is max. 0.2 wt. %. Preferably, carbonate as $CO_2$ is 0.2 wt. % max. Furthermore, generally, aldehydes are max. 5 ppm (by weight) and/or insoluble matter is max. 20 ppm (by weight). Generally, $PO_4$, Ca, Fe, Al, Mg, Na and K are each max. 0.5 ppm. Cu, Zn, Cr and Ni are generally each max. 0.2 ppm (all ppm by weight). The same applies for the urea-comprising stream suitable for use as or for preparation of DEF prepared in the inventive process.

For DEF precursor solution, the impurities are preferably such that said impurities levels are obtained after dilution by adding water to the urea content of the DEF specification (e.g. by dilution by adding water to 32.5 wt. % urea). The above purity level values are given at 32.5 wt. % urea. Generally, it is desired and advantageous that the purity exceeds these limits, e.g. that the DEF product or the DEF precursor has higher purity.

The purified urea solution from the treatment section and the DEF product and/or the DEF precursor product, e.g. from the DEF production unit, preferably have an alkalinity as $NH_3$ of max. 0.2 wt. %; biuret max. 0.3 wt. %; $PO_4$, Ca, Fe, Al, Mg, Na and K each max. 0.5 ppm by weight; and Cu, Zn, Cr and Ni each max. 0.2 ppm by weight, and a urea content of at least 32.5 wt. %. The same preferred levels apply for the urea-comprising stream suitable for use as or for preparation of Diesel Exhaust Fluid prepared in the inventive process.

The purified urea solution from the treatment section and the DEF product and/or the DEF precursor product, e.g. from the DEF production unit, preferably have an alkalinity as $NH_3$ of max. 0.2 wt. %; biuret max. 0.3 wt. %; $PO_4$, Ca, Fe, Al, Mg, Na and K each max. 0.5 ppm by weight; and Cu, Zn, Cr and Ni each max. 0.2 ppm by weight, calculated on the basis of 32.5 wt. % urea by adding water as necessary, and an actual urea content of at least 32.5 wt. %. The same preferred levels apply for the urea-comprising stream suitable for use as or for preparation of DEF prepared in the inventive process.

Advantageously, the second stream has a lower metal content relative to urea (wt. % relative to urea) than the stripped urea solution. Preferably, the relatively lower temperatures in the treatment section than in the HP stripper contribute to maintaining this relatively lower metal content which is advantageous for making DEF or DEF precursor.

In some embodiments, the treatment section operates entirely at temperatures lower than 170° C. or lower than 165° C. or even lower than 160° C.

Preferably, the treatment section yields a urea solution with at least 32.5 wt. % urea and with biuret max. 0.3 wt. % and/or $NH_3$ max. 0.2 wt. %, calculated on the basis of 32.5 wt. % urea, i.e. for urea solutions with a higher urea content, by adding water as necessary to arrive at 32.5 wt. % urea.

The invention in an aspect provides urea production process, wherein a urea synthesis stream in split into a first part and a second part. The urea production process is preferably carried out in a plant according to the invention, and all preferences regarding the plant apply equally to the process carried out in a plant according to the invention. The first part is stripped in an HP stripper, recovered in a recovery section, and processed into a first urea-containing product, with as preferred features the preferences and details as described in connection with the plant. The recovery section comprises one or more recovery section decomposers, with details as discussed in connection with the plant.

In the process, the second stream is sent to a treatment section without passing through the HP stripper. The treatment section comprises one or more treatment section decomposers, which operate separately from and in parallel to the one or more recovery section decomposers. The treatment section produces a urea-comprising stream that is suitable for use as DEF, or that is suitable for preparation of DEF by dilution with water. The urea-comprising stream is preferably the same as the purified urea solution discussed in connection with the plant.

The urea-comprising stream is for instance supplied to a DEF production unit, where the urea-comprising stream is for instance diluted by adding clean water, or is for instance subjected to dry flashing. The dry flashing product is a DEF precursor which can be converted into DEF by adding clean water. The urea-comprising stream at the inlet of the dry flashing unit typically already has sufficiently high purity that it can be converted to DEF by adding water. Details of the dry flashing are the same discussed in connection with the plant. Added clean water is for instance clean process condensate from a wastewater treatment section of the urea plant.

The treatment section and the processing therein has as preferred features the same preferences and details as described in connection with the plant.

Preferably, the urea-comprising stream obtained from the treatment section comprises at least 32.5 wt. % urea and preferably has, at 32.5 wt. % urea, alkalinity as $NH_3$ of max. 0.2 wt. %; biuret max. 0.3 wt. %; $PO_4$, Ca, Fe, Al, Mg, Na and K each max. 0.5 ppm by weight; and Cu, Zn, Cr and Ni each max. 0.2 ppm by weight. These impurity limits are calculated on the basis of 32.5 wt. % urea, i.e. on the basis of adding water as necessary to the urea solution to obtain 32.5 wt. % urea.

Preferably, the recovery section comprises a recovery section LP decomposer and the treatment section comprises a separate treatment section LP decomposer. Preferably these LP decomposers are arranged in parallel. Hence, the process in particular involves subjecting the urea solution in the treatment section to decomposition in a dedicated LP decomposer.

Preferably, in the process neither stripped urea solution from the HP stripper nor urea solution obtained from the stripped urea solution from the HP stripper is combined with the second stream or with urea solution originating from said second stream. In other words, preferably no urea solution is supplied from the HP stripper or from the recovery section to the treatment section. Thereby urea solution in the treatment section is not contaminated with any impurities in the stripped urea solution from the HP stripper.

Preferably, the plant accordingly does not comprise a flow line for such transport of urea solution. Preferably, the plant does not include a flow line for stripped urea solution from the HP stripper, or for urea solution obtained from the stripped urea solution from the HP stripper, to a flow line or unit in the plant which receives the second stream or to a flow line or unit which receives urea solution originating from said second stream.

Preferably, less than 1.0 wt. %, preferably 0 wt. % of the urea in the DEF product, DEF precursor product, and urea stream from the treatment section, originates from the HP stripper.

The invention in an aspect also provides a method of modifying an existing urea plant of the stripping type comprising a synthesis section comprising a reaction zone, a condensation zone, and a HP stripper, and a recovery section. The existing plant for example also comprises an evaporation section and a waste water treatment section. The method comprises adding to the existing plant a flow splitter and a treatment section. The flow splitter is arranged for dividing a urea synthesis stream from the reaction zone into a first part and a second part, the first part being supplied to the HP stripper. The treatment section is adapted for processing said second part. The recovery section comprises a recovery section LP decomposer and the added treatment section preferably comprises a separate treatment section LP decomposer, arranged in parallel to the recovery section LP decomposer in the modified plant. Preferably, the method also involves adding a steam stripper comprised in the treatment section downstream of the treatment section LP decomposer. The steam stripper is configured for injecting steam into the urea solution that is purified in the treatment section. The modified plant is preferably a urea production plant according to the invention. The method preferably also involves adding a DEF production unit downstream of the treatment section, such as a unit for diluting the urea solution from the treatment section or for subjecting the urea solution to dry flashing. Preferably the method involves adding a flow line for clean process condensate from the waste water treatment section to the DEF production unit. All details and preferences for the inventive urea production plant also apply to the modified plant of the method.

Figure 1:
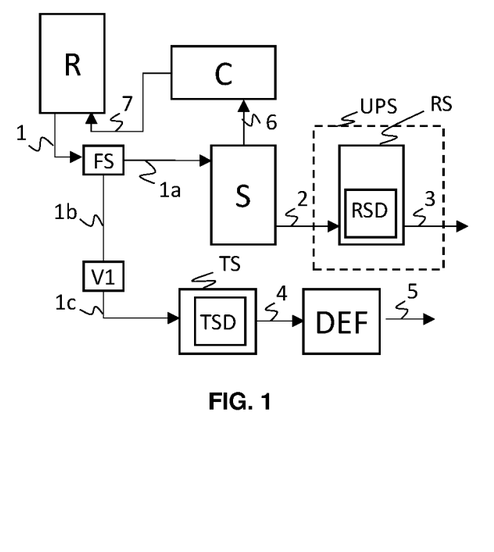
FIG. 1 schematically illustrates an example urea plant and process according to the invention.

FIG. 1 schematically illustrates an example urea plant and process according to the invention comprising a HP synthesis section comprising a reactor (R), a HP stripper (S), a carbamate condenser (C) and a flow splitter (FS). Urea synthesis solution (1) from the reactor (R) is divided in the flow splitter (FS) in a first stream (1a) comprising urea that is supplied to the HP stripper (S) and a second stream (1b) also comprising urea.

The gas stream (6) from the HP stripper (S) is supplied to the carbamate condenser (C) and the liquid comprising carbamate (7) from the condenser is supplied to the reactor (R). $NH_3$ feed and $CO_2$ feed are also supplied to the synthesis section. Inert gases are removed from the synthesis section (not shown).

Stripped urea solution (2) is supplied to a recovery section (RS) where the urea content of the solution (2) is increased by removal of $NH_3$, $CO_2$ and ammonium carbamate to give urea stream (3). The recovery section (RS) comprises at least one recovery section decomposer (RSD), which is e.g. a heat exchanger for heating the urea solution. The recovery section (RS) is comprised in the urea processing section (UPS). The urea processing section (UPS) may further comprise, e.g., an evaporation section and a finishing section downstream of the recovery section.

The second stream (1b) is expanded in an expansion device, e.g. valve (V1), and supplied as expanded stream (1c) to a treatment section (TS) where it is processed into a high purity urea solution (4). The high purity urea solution (4) is used for making DEF and/or DEF precursor (5) in the DEF production unit (DEF). In practice, the plant includes further units, flow lines, and elements, such as additional valves and control valves. The treatment section (TS) comprises at least one treatment section decomposer (TSD) which is arranged in parallel to the recovery section decomposer (RSD).

Figure 2:
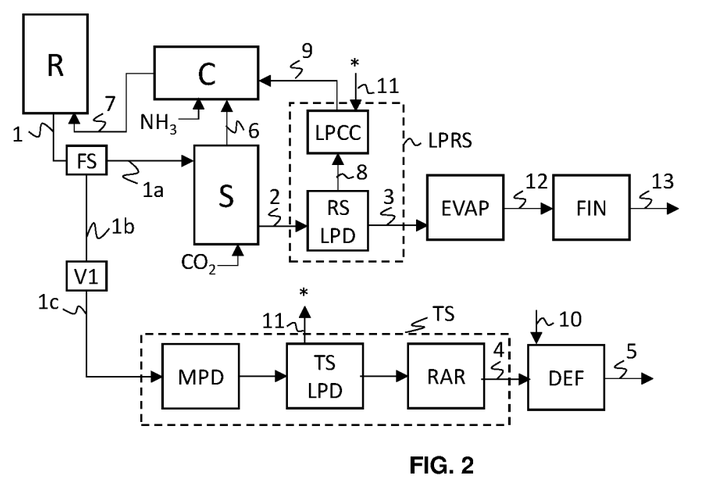
FIG. 2 schematically illustrates an example urea plant and process according to the invention.

FIG. 2 schematically illustrates an example urea plant and process according to the invention with a $CO_2$ HP stripper (S). References are the same as in FIG. 1 unless otherwise specified. The reactor (R) contains a downcomer connected to the liquid outlet (1) and a separate gas outlet at the top (not shown). Stripped urea solution (2) is supplied directly to a recovery section LP pressure decomposer (RSLPD) comprised in a LP recovery section (LPRS). Gas (8) from the LP decomposer (RSLPD) is condensed in an LP carbamate condenser (LPCC) and the resulting carbamate solution (9) is supplied to the HP carbamate condenser (C) which also receives the $NH_3$ feed. The treatment section (TS) comprises an MP decomposer (MPD) and an LP decomposer (TSLPD) arranged in series, for treating the expanded second urea stream (1c). Gas (11) from the LP decomposer (TSLPD) is condensed for instance in a dedicated LP carbamate condenser (not shown) or, as illustrated, supplied to the LP carbamate condenser (LPCC) of the LP recovery section (LPRS). The treatment section LP decomposer (TSLPD) and the recovery section LP decomposer (RSLPD) are separate units arranged in parallel. The urea processing section may further comprise an evaporation section (EVAP) for concentrating the LP urea solution (3) from the recovery section LP decomposer (RSLPD) by water evaporation to form a urea melt (12). The urea melt (12) is supplied to a finishing section (FIN), e.g. a prilling tower or a granulator, to form solid urea product (13).

The treatment section (TS) further comprises a residual ammonia removal unit (RAR). The high purity urea solution (4) is supplied from residual ammonia removal unit (RAR) to the DEF production unit (DEF), which is a dilution unit with an inlet (10) for clean water.

Advantageously, the precursor solution (4) for the production of DEF has not been exposed to the typical high temperature conditions in the HP stripper (S) and therefor avoids the biuret formation and metal uptake resulting from these conditions and from corrosion taking place in the HP stripper (S).

In practice, the plant includes further units, flow lines, and elements, such as additional valves and control valves.

Figure 3:
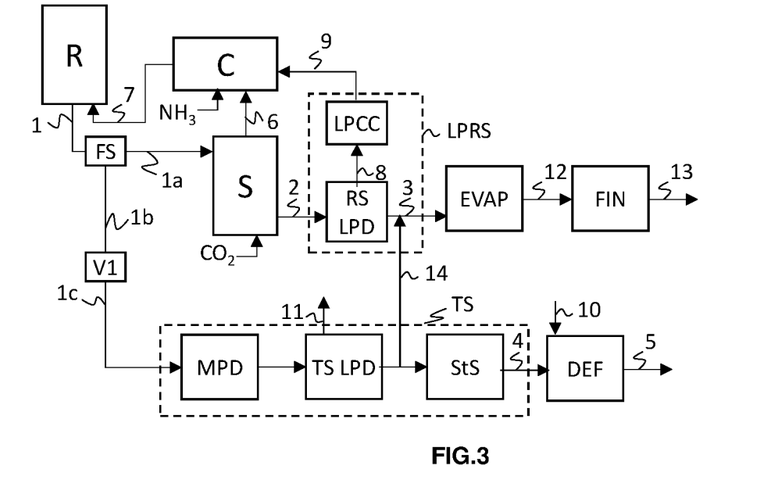
FIG. 3 schematically illustrates an example urea plant and process according to the invention.

FIG. 3 schematically illustrates an example urea plant and process according to the invention. References are the same as in FIG. 2 unless otherwise specified. The residual ammonia removal unit (RAR) is implemented as a steam stripper (StS). The steam stripper (StS) is a vessel for injection of steam into the urea solution to effect stripping. The steam stripper (StS) has supply line for steam (not shown) and a gas outlet connected to a condenser (C) (not shown). The plant further comprises a flow line (14) for LP urea solution from the treatment section LP decomposer (TSLPD) to the evaporation section (EVAP) which can be used if there is low demand for DEF and/or high demand for solid urea product, or in case of upset conditions.

Other configurations of the preferred liquid flow connection from the treatment section (TS) to the evaporation section (EVAP) are also possible, e.g. through the recovery section LP decomposer (RSLPD) (not shown) or by supplying the urea solution (4) to the evaporation section (EVAP) (not shown).

In summary, embodiments of the invention provide a urea plant and urea production process of the stripping type that are adapted for making Diesel Exhaust Fluid (DEF) or a precursor thereof in a DEF production unit downstream of a treatment section. The treatment section receives a part of the urea synthesis stream from a reaction zone, in particular bypassing the HP stripper.

As used herein, HP (high pressure) indicates a pressure of e.g. at least 100 bara, e.g. 120-250 bara, or e.g. 110-160 bara, MP (medium pressure) indicates a pressure of e.g. 15-80 bara, 20-80 bara, and LP (low pressure) indicates a pressure of e.g. 1-10 bara, e.g. 4-10 bara; these pressure ranges are for process streams, in particular for solutions, and not necessarily the same for steam and heating fluids. The abbreviation "bara" means bar absolute. Pressures are absolute pressures unless indicated otherwise.

The term 'typically' as used herein indicates features that are frequently used, but are not mandatory.

As used herein, "carbamate" refers to ammonium carbamate.

The terms 'typical', 'generally' and 'in particular' are used to indicate features that can be used in some embodiments but that are not mandatory in all embodiments. Preferred features are not mandatory.

The N/C ratio as used herein for urea solutions at the reaction zone outlet reflects the composition of the so-called initial mixture before urea production, consisting only of $NH_3$, $CO_2$ and $H_2O$, as the term is used in the art of urea plants, and is the molar ratio. The N/C ratio for gas streams indicates the molar ratio of $NH_3$ to $CO_2$. The N/C ratio for a carbamate condenser indicates the molar ratio of $NH_3$ to $CO_2$ at the outlet for carbamate solution.

The invention claimed is:

1. A urea production plant for producing a first urea-containing product and a second urea-containing product, wherein the second urea-containing product is Diesel Exhaust Fluid (DEF) or DEF precursor, the plant comprising a high pressure (HP) synthesis section comprising a reaction zone, a high pressure stripper, a condensation zone, and a flow splitter adapted for dividing a urea synthesis stream from said reaction zone into a first stream and a second stream, and a flow line for said first stream to said HP stripper, the plant further comprising:
 a urea processing section for processing stripped urea solution from said HP stripper into said first urea-containing product, the urea processing section comprising a recovery section comprising one or more recovery section decomposers for processing said stripped urea solution and an outlet for the first urea-containing product;
 an expansion device for expanding said second stream to give an expanded second stream;
 a treatment section comprising one or more treatment section decomposers for purifying said expanded second stream into a purified urea solution, wherein the one or more treatment section decomposers are arranged in parallel to the one or more recovery section decomposers; and
 a DEF production unit for producing DEF and/or DEF precursor from said purified urea solution, the DEF production unit comprising an outlet for the DEF and/or DEF precursor.

2. The urea production plant according to claim 1, wherein the treatment section comprises a treatment section low pressure (LP) decomposer and the recovery section comprises a recovery section low pressure (LP) decomposer parallel to the treatment section LP decomposer.

3. The urea production plant according to claim 1, wherein the treatment section comprises a steam stripper for stripping urea solution by injection of steam.

4. The urea production plant according to claim 1, wherein the DEF production unit comprises an inlet for adding clean water to the purified urea solution.

5. The urea production plant according to claim 1, wherein the DEF production unit comprises a dry flashing unit.

6. The urea production plant according to claim 1, wherein the plant does not include a flow line for stripped urea solution from the HP stripper or for urea solution obtained from the stripped urea solution from the HP stripper to a flow line or unit in the plant which receives the second stream or which receives urea solution originating from said second stream.

7. The urea production plant according to claim 1, wherein at least one of the one or more recovery section decomposers is the recovery section LP decomposer, wherein the recovery section optionally comprises a medium pressure (MP) decomposer between the outlet for stripped urea solution of the HP stripper and said recovery section LP decomposer; wherein the plant further comprises a low pressure (LP) carbamate condenser for condensing gas from said recovery section LP decomposer, wherein said LP carbamate condenser is optionally also used for condensing gas from a treatment section LP decomposer comprised in said treatment section.

8. The urea production plant according to claim 1, wherein the HP stripper uses at least a part of the $CO_2$ feed for stripping.

9. A urea production plant according to claim 1, wherein the urea processing section comprises an evaporation section for converting urea solution into urea melt downstream of the recovery section and a liquid flow connection for urea solution from the treatment section to the evaporation section.

10. The urea production plant according to claim 1, wherein the stripper is a shell-and-tube heat exchanger comprising stripper tubes made of duplex stainless steel.

11. A urea production process comprising:
 splitting a urea synthesis stream into a first part and a second part;
 stripping the first part in a high pressure (HP) stripper, recovering in a recovery section comprising one or more recovery section decomposers, and processing into a first urea-containing product;

sending the second part to a treatment section comprising one or more treatment section decomposers without passing through the HP stripper; and operating the one or more treatment section decomposers separately from and in parallel to the one or more recovery section decomposers and producing from the treatment section a urea-comprising stream that is suitable for use as Diesel Exhaust Fluid (DEF) or for preparation of DEF by diluting with water.

12. The process according to claim 11, wherein the urea-comprising stream at 32.5 wt. % urea has an alkalinity as $NH_3$ of max. 0.2 wt. %; biuret max. 0.3 wt. %; $PO_4$, Ca, Fe, Al, Mg, Na and K each max. 0.5 ppm by weight; and Cu, Zn, Cr and Ni each max. 0.2 ppm by weight.

13. The process according to claim 11, wherein the recovery section comprises a recovery section low pressure decomposer and the treatment section comprises a treatment section low pressure decomposer arranged parallel to the recovery section low pressure decomposer.

14. The process according to claim 11, carried out in a plant according to claim 1.

15. The urea production process according to claim 11, wherein no urea solution is supplied from the HP stripper to the treatment section.

16. The urea production process according to claim 11, wherein no urea solution is supplied from the recovery section to the treatment section.

17. The urea production process according to claim 11, wherein the first urea-containing product is a urea fertilizer product.

18. A method of modifying an existing urea plant of the stripping type comprising a high pressure (HP) synthesis section comprising a reaction zone, a condensation zone, and a HP stripper, and a recovery section, wherein the recovery section comprises a recovery section low pressure decomposer, the method comprising adding to the existing plant:

a flow splitter for dividing a urea synthesis stream from the reaction zone into a first part and a second part, the first part being supplied to the HP stripper;

a treatment section for processing said second part, wherein the treatment section comprises a treatment section low pressure (LP) decomposer in parallel to the recovery section low pressure (LP) decomposer.

19. The method of claim 18, wherein the added treatment section comprises a steam stripper.

* * * * *